United States Patent [19]
Jones et al.

[11] 3,949,595
[45] Apr. 13, 1976

[54] AUTOMATIC ANTIKNOCK ADJUSTMENT

[75] Inventors: John T. Jones, Ardsley; William C. Ludt, Yonkers; Hudson W. Kellogg, Dobbs Ferry, all of N.Y.

[73] Assignee: Ethyl Corporation, New York, N.Y.

[22] Filed: June 23, 1964

[21] Appl. No.: 377,192

Related U.S. Application Data

[63] Continuation-in-part of Ser. Nos. 299,583, Aug. 2, 1963, abandoned, and Ser. No. 205,015, June 25, 9162, Pat. No. 3,383,904.

[52] U.S. Cl................. 73/35; 73/421 R; 73/422 R
[51] Int. Cl.² ........................................ G01L 23/00
[58] Field of Search ....... 73/422, 35, 113, 114, 421; 123/139.16, 136

[56] References Cited
UNITED STATES PATENTS
3,274,985  9/1966  Traver et al. ...................... 73/35 X

*Primary Examiner*—James J. Gill

[57] ABSTRACT

In the blending of gasoline a knock testing engine is automatically fed samples of the blended fuel and a standard fuel. The blending is controlled to maintain the knock intensity of the blended fuel at a standard value. Fuel sampling means are provided to minimize the time lag between blending and knock intensity determination.

10 Claims, 6 Drawing Figures

INVENTORS:
JOHN T. JONES
WILLIAM C. LUDT
HUDSON W. KELLOGG

BY Donald L. Johnson
ATTORNEY

INVENTORS:
JOHN T. JONES
WILLIAM C. LUDT
HUDSON W. KELLOGG

BY Donald L. Johnson
ATTORNEY

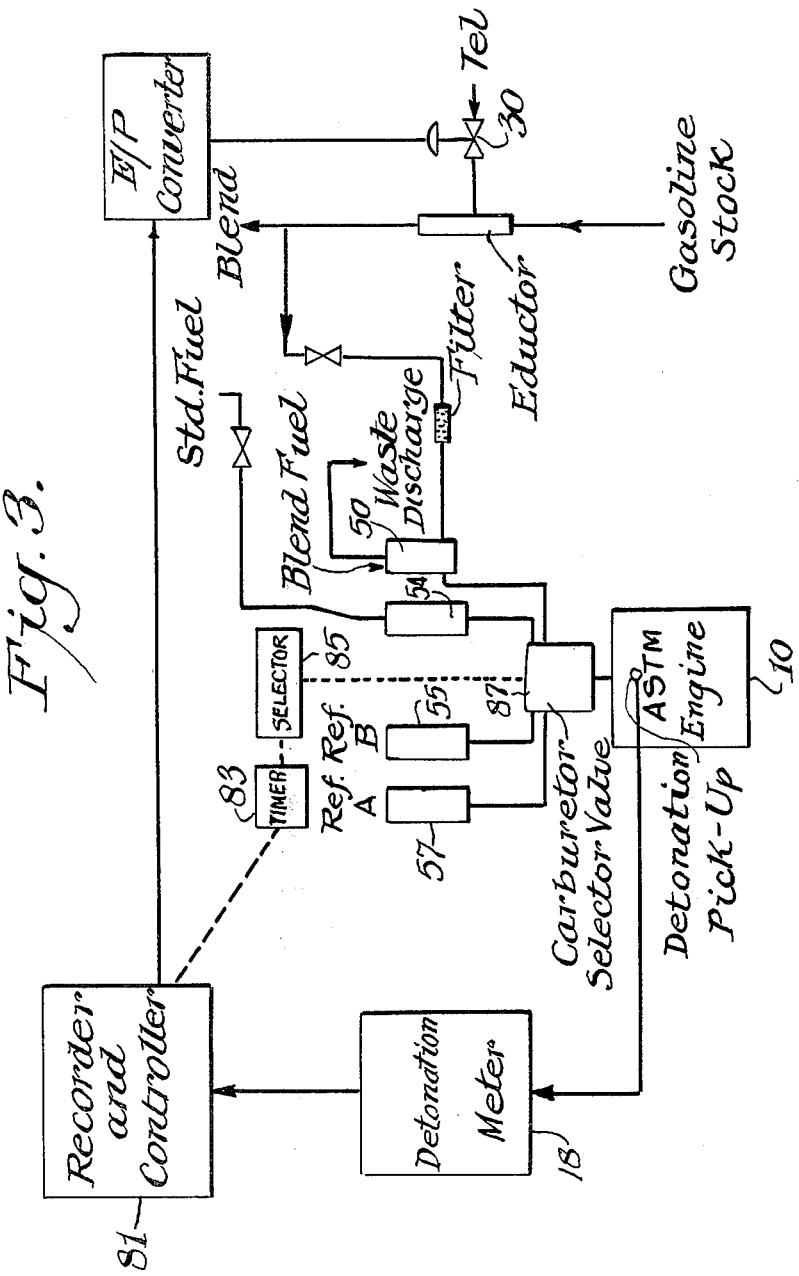

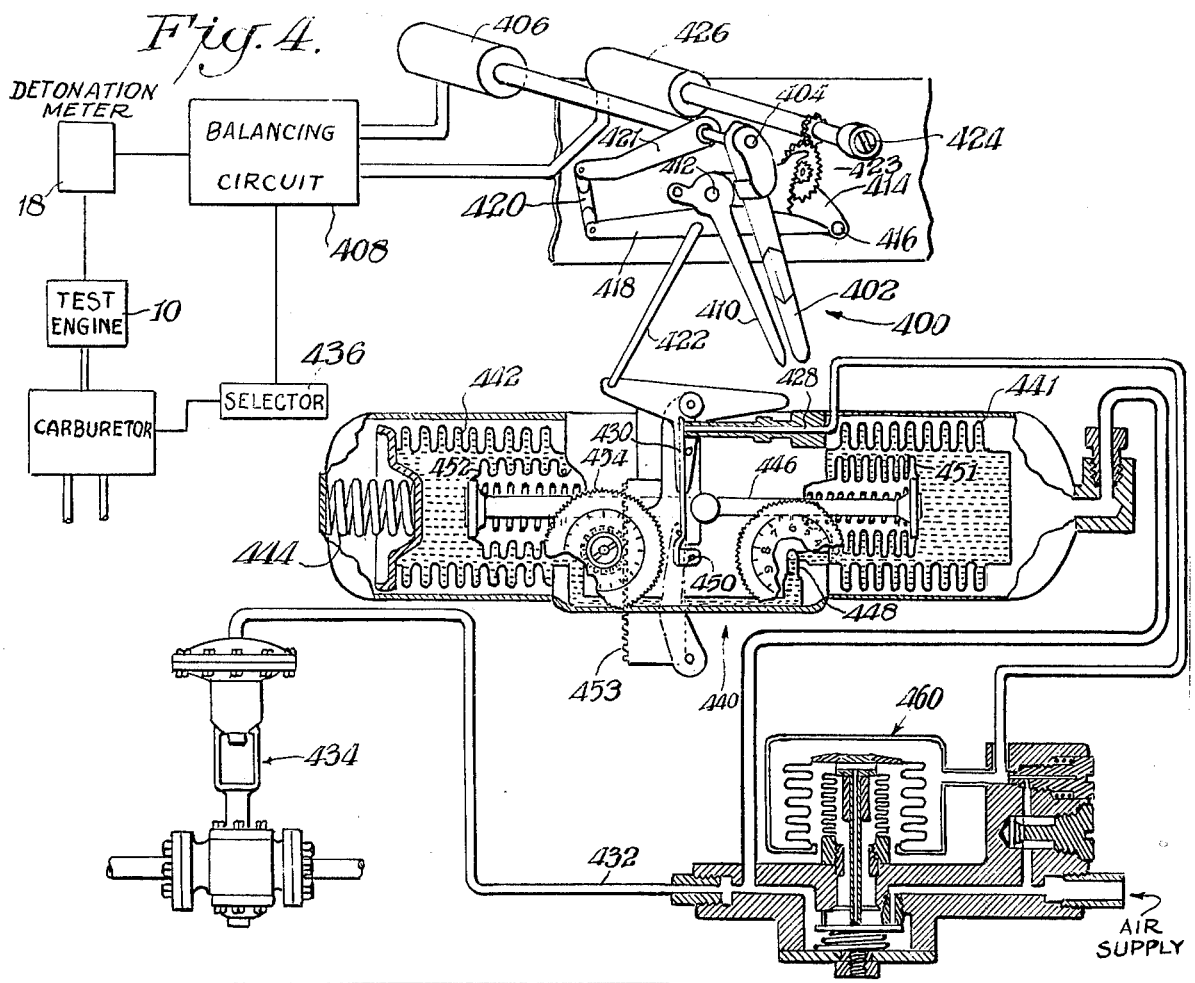
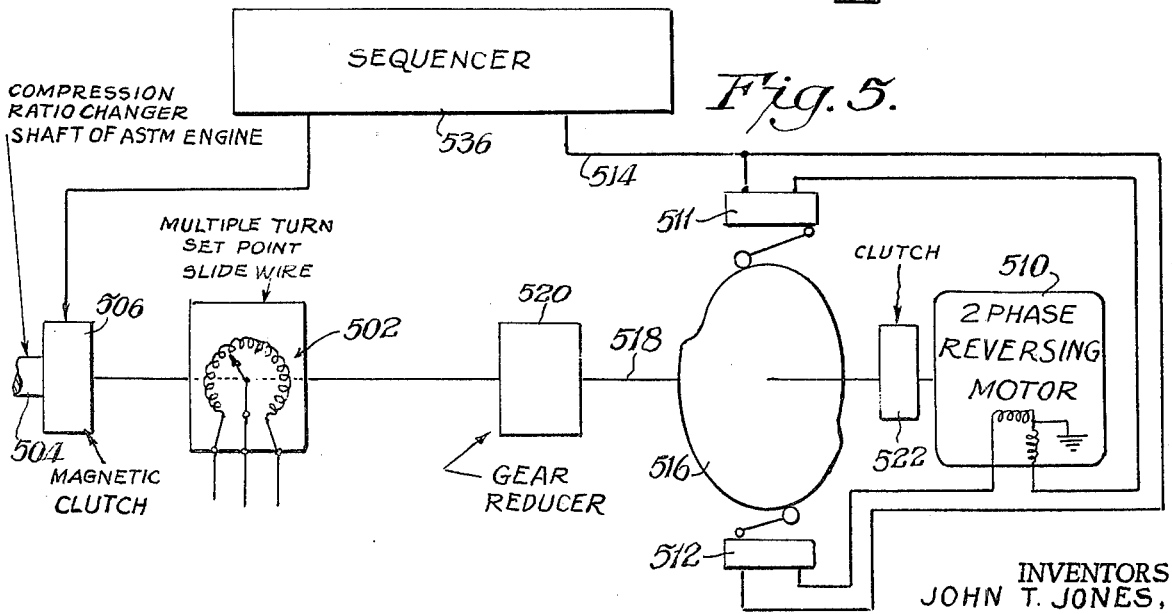

AUTOMATIC ANTIKNOCK ADJUSTMENT

The present application is in part a continuation of application Ser. No. 299,583 filed Aug. 2, 1963 (and subsequently abandoned), and of application Ser. No. 205,015 filed June 25, 1962 (U.S. Pat. 3,383,904, granted May 21, 1968).

The present invention relates to the adjustment of the antiknock ratings of gasoline and the like.

Among the objects of the present invention is the provision of novel apparatus and method for automatically adjusting the antiknock ratings of the above type of fuels.

One of the problems of automatic gasoline blending is the withdrawal of samples of the blended gasoline and the prompt supplying of these samples to a test engine at a selectable liquid level or height so as to permit the sample to be accurately carbureted into the engine with very little time delay.

According to the present invention the sampling and leveling is readily accomplished with a relatively small container having a horizontally directed inlet in its lower portion for connection to a source of the liquid being sampled, a horizontally directed outlet also in its lower portion for connection to a testing means, a suction tube projecting into the interior of the container from its upper portion for sucking out excess liquid and thereby defining a level for the liquid in the container, and a baffle between the outlet and the inlet.

The suction tube can desirably be threaded through the top of the container and provided with a rotary connection through which it is connected to a suction line while the tube is capable of being rotated and thereby threaded up and down in the container. It is helpful to have a vent opening establishing open communication between the fuel in the container and the outside air if the interior of the container is to be maintained at atmospheric pressure. The vent can be incorporated in the rotary connection as by merely making it a loose fit in the top of the container.

It is also very helpful to have the walls of the container transparent so that the flow of sampling liquid can be readily monitored.

The flow of sampling liquid into the container should be between about 300 and 500 milliliters per minute so as to provide liquid at a rate fast enough to rapidly follow the characteristics of the principal stream of liquid being adjusted, without creating so much turbulence in the container as to prevent it from forming an accurate controllable level. To this end the horizontally directed inlet and outlet can be at the very bottom of the container, and desirably there is a baffle between them. With this construction the inlet and outlet can be aligned on opposite sides of the container, the baffle serving to circulate the incoming liquid through the entire contents of the container before it flows out to the engine.

The apparatus of the present invention is highly suited for automatically monitoring and/or adjusting the octane rating of a fuel stream in a fuel supply system such as in a gasoline refinery. In such an arrangement the automatic knock measuring equipment includes sampling means connected for receiving samples of a fuel stream to be adjusted, and also includes output elements that periodically develop a correction signal corresponding to the difference between the antiknock rating of the sample and a predetermined desired rating. The correction signal can then be used to operate adjusting elements such as a mixing valve that controls the amount of high antiknock blending stock to the fuel system, and can adjust the fuel flow in a manner that reduces the magnitude of the correction signal. The high antiknock blending stock can be a refinery stock or it can merely be an antiknock concentrate such as tetraethyl lead with or without scavenger and diluent, or it can be a mixture of refinery stock with antiknock.

For best results the apparatus is arranged to automatically switch the fuel supply to the test engine periodically so that the test engine will operate on a standard or reference fuel sufficiently frequently that any departure in the operation of the engine can be promptly detected and compensated for.

To this end the automatic measuring equipment can have an indicator to show the relative rating of a fuel sample, a standard reference control, means for originally setting the indicator at a predetermined portion of its range, and automatic compensating mechanism connected to periodically cause the measuring equipment to measure the antiknock rating of a standard fuel and to adjust the indicator so that the rating of the standard fuel corresponds with the standard reference control to compensate for drift of the automatic measuring equipment.

The foregoing as well as additional objects of the present invention will be more fully appreciated from the following description of several of its exemplifications, reference being made to the accompanying drawings wherein:

FIG. 3 is a view similar to FIG. 1 of a modified form of automatic antiknock adjustment apparatus typical of the present invention;

FIG. 4 is another view similar to FIG. 1 of a further and more deep-seated modification of automatic blending apparatus representative of the present invention;

FIG. 5 is a schematic illustration of an accessory unit that can be used with the automatic apparatus of the present invention.

Figure 1:
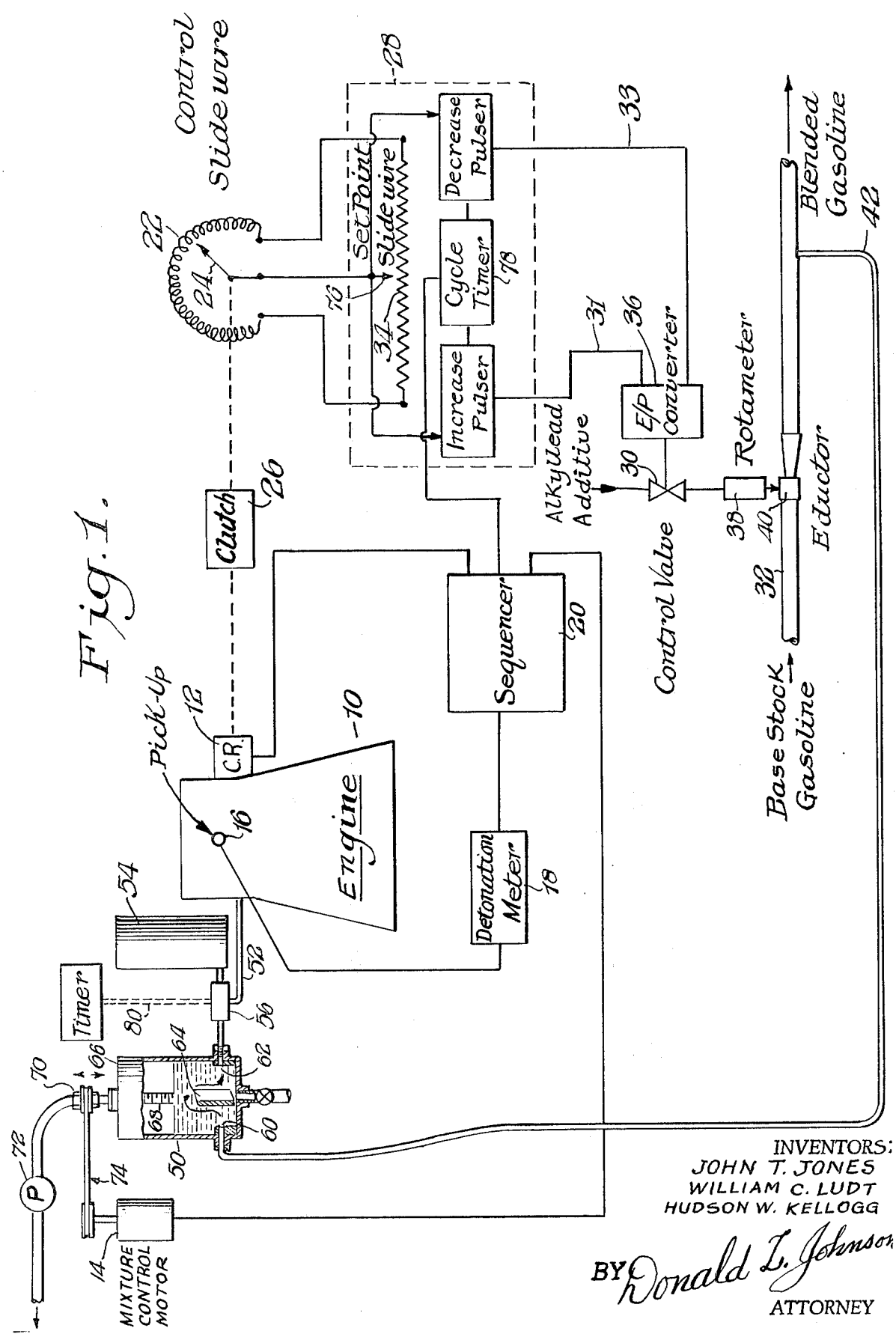
FIG. 1 is a partially schematic representation of an automatic apparatus for blending antiknock additives with gasoline pursuant to the present invention.

Referring to the drawings, the apparatus of FIG. 1 includes a test engine indicated at 10 which can be of the standard type such as illustrated and described in the 1960 ASTM Manual for Rating Fuels by Motor and Research Methods, published by the American Society for Testing and Materials, Philadelphia, Pa.

The engine has a reversible type electric motor 12 connected to vary the compression ratio of the test engine, and another such motor 14 connected to change the fuel-to-air ratio of the combustion mixture supplied to the test engine.

As in the usual test engine construction, a detonation pick-up 16 is provided so as to develop an electrical signal varying in intensity in accordance with the intensity of the detonation or knock that occurs during the operation of the test engine. In the apparatus of FIG. 1 the signals so produced are delivered to an amplifier 18 which can indicate the signal strength on a meter. The amplified signals then go to a sequencer or programmer 20 which controls the engine for the purpose of making a search of compression ratios and fuel-to-air ratios and determining the compression ratio and fuel-to-air ratio that produces a maximum knock of standard intensity. The resulting compression ratio is indicated by a compression ratio control slidewire 22 having a slider 24 connected for movement with the compression ratio motor 12. A clutch 26 can be inserted in the connection between the slider 24 and the motor 12, to enable the slider to be shifted to any desired portion of the slidewire range for any reference compression ratio.

A deviation computer 28 is connected to the control slidewire 22 and operates a control valve 30 to control the flow of alkyllead additive or other antiknock-improving liquid to a gasoline blending stream 32. The deviation computer can be of the deviation proportion pulse control type and include a set point slidewire 34 as described in the foregoing earlier patent applications, to provide variable-length electrical pulses in lines 31, 33. Instead of having the pulses directly operate the control valve 30, the control valve can be of the more popular pneumatically-operated variety with the pulses supplied to an electric-to-pneumatic signal converter 36 that in turn develops a pneumatic pressure fed to the valve. Suitable electric-to-pneumatic converters, some connected to operate valves, are shown for example in the paper "Electric Actuators: Examination and Evaluation" in the ISA Journal issue of August 1957, pages 326 to 331. The Fisher Governor Co. type 543 electro-pneumatic transducer is also suitable. The rate of flow of the antiknock-improving liquid can be measured or indicated by a rotameter 38, if desired.

Blending of the antiknock-improving liquid with the gasoline base stock is conveniently carried out with an eductor 40. A sample line 42 opening into the blend conduit downstream of the eductor withdraws a small amount of the blended product and delivers it to a carburetor bowl 50 for carbureting into the intake fuel line 52 of the test engine. Another bowl 54 can be arranged to supply a standard or reference fuel to have its antiknock characteristics compared with the blended samples, a selector valve 56 enabling either carburetor bowl to be connected to supply the test engine.

Bowl 50 is in the form of a relatively narrow container with a horizontally directed inlet 60 and a horizontally directed outlet 62 in its lower portion. The inlet and outlet are aligned but between them is a baffle 64 that prevents the incoming fuel from flowing directly out without mixing with and displacing the body of fuel in the bowl and also to prevent a ram effect on the carburetor jet because of the relatively high fuel inlet flowrate.

Through the top 66 of the container there is threadedly received a suction tube 68 connected as by a swivel connector 70 to the intake of a suction pump 72 which can discharge to waste or to the blended gasoline line. Suction tube 68 is connected as by pulley around belt assembly 74 to the fuel-to-air ratio controlling motor 14, so that rotation of the motor will raise or lower the height of the lower end of the tube. The walls of container 50 are advantageously transparent so that its contents can be observed. The outlet of pump 72 can also have a pressureoperated switch that warns when the pump is not operating. A very effective configuration of container is cylindrical with a diameter of nine-sixteenths inches and an overall height of 5 inches such as the standard ASTM engine carburetor sight glass and body. A sample flow of 300 to 500 milliliters per minute through such a container gives very effective sampling.

In operation the apparatus of FIG. 1 has its deviation computer set as by adjustment of a set point slidewire wiper 76 it contains, to correspond to the position of the control slidewire 22 representing the compression ratio that gives the standard knock intensity when the engine is fed with the standard or reference fuel at the fuel-to-air ratio producing maximum knock. The engine is then supplied with the blended fuel and the sequencer effects variations of compression ratio and fuel-to-air ratio until under maximum knock conditions the compression ratio produces a knock of standard intensity. The sequencer then actuates the cycle timer 78 of the computer 28 which in turn determines the difference between the control slidewire, representing the compression ratio for the blend, and the set point slidewire, representing the compression ratio for the standard or reference fuel. If there is a difference an appropriate pulse is delivered to adjust the control valve in the compensatory direction. If there is no difference, indicating that the blend has the desired antiknock value, no compensating pulses are generated.

Figure 2:
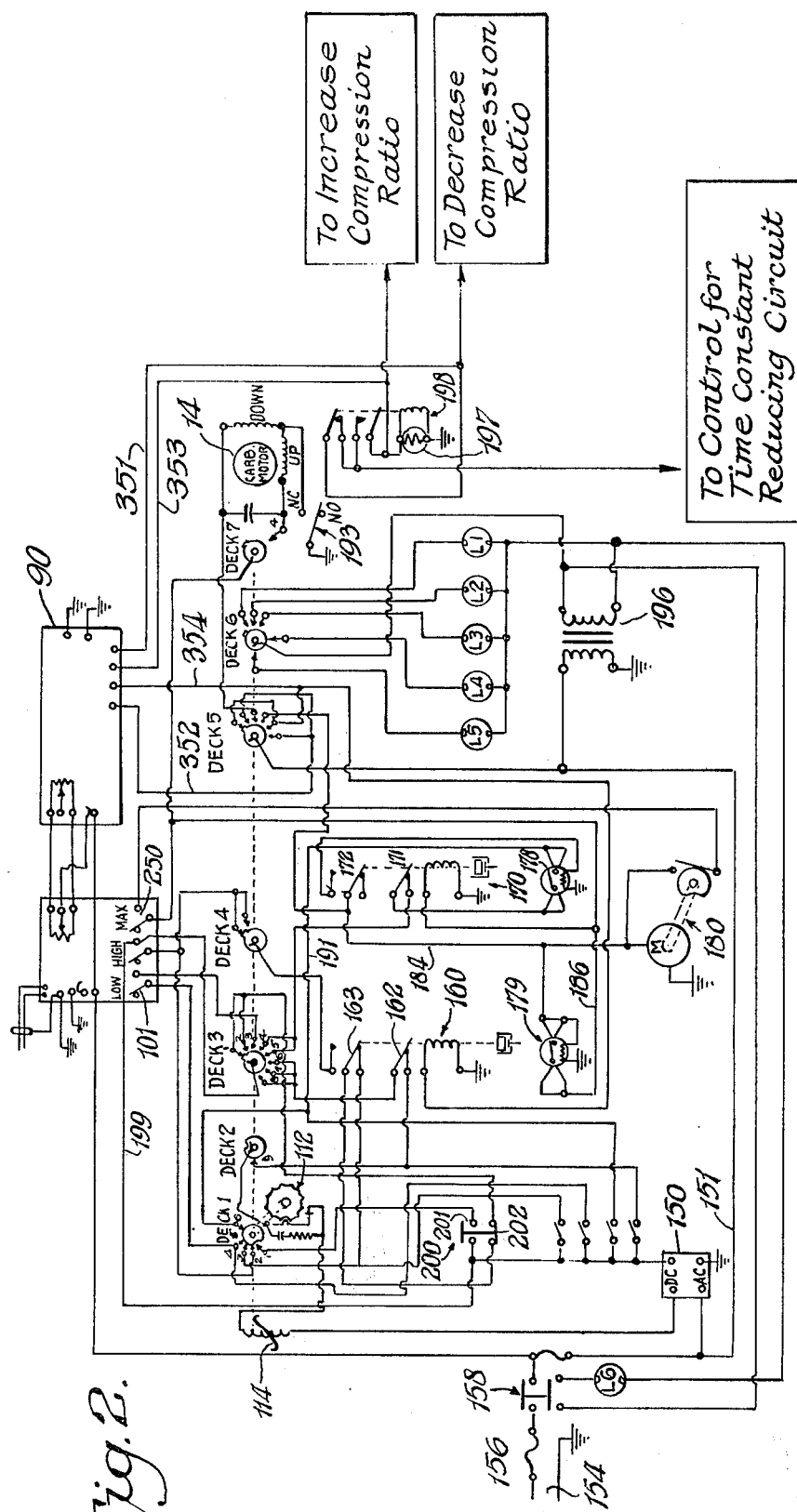
FIG. 2 is a circuit diagram of a portion of the apparatus schematically shown in FIG. 1.

The sequencer of FIG. 1 can be identical to that illustrated in the prior applications, or it can be in the form shown in FIG. 2 which is generally similar and has its corresponding parts similarly numbered. The construction of FIG. 2 has a 12-position rotary stepping switch assembly 112 operated by a stepping solenoid 114 from the dc output of rectifier 150. The rotary switch has seven decks and is shown in the position from which it starts a sequence cycle of clockwise steps. Decks 1 and 2 are interrelated, steps 1 through 6 being on deck 1 and steps 7 through 12 on deck 2. The switch is brought to the illustrated position by operating start switch 200, shown in non-operated condition, and holding that switch operated until the rotary switch finishes stepping. The solenoid power circuit through contacts 201 of switch 200 and step 1 contact of deck 1 is then interrupted. In this condition the winding of relay 160 is energized through ac bus 151 and step 1 contact of deck 5, and shifts its armatures away from the de-energized position shown. This relay is energized without delay but upon de-energization does not return to the illustrated position until the expiration of a pre-set time delay which can be 35 to 40 seconds or thereabouts.

As soon as the start switch 200 is released, it returns to the illustrated condition and its lower contacts 202 complete a solenoid energizing circuit through step 2 contact of deck 1, step 1 contact of deck 4, upper armature 163 of relay 160, step 1 contact of deck 3 and return lead 199. The stepping switch then steps to the next or initial compression ratio search position.

In the compression ratio search position pulses are delivered from control device 90 to the decrease or increase pulse output lines 351, 353 to bring the compression ratio of the test engine to the point that produces knock of standard intensity. A pulse is supplied to line 354 whenever there is either an increase or decrease pulse, and thus re-energizes relay 160 momentarily so that it must restart its time delay cycle. Energizing lead 352 connected from steps 2 and 6 of deck 5 to the control device terminals supplies the current that is pulsed when needed, so that no pulses can be delivered by the control device when the stepping switch 112 is in other positions. In addition a time constant reducing control is also supplied with pulses either from line 354 or as shown through relay 198 so that a long pulse either of the decrease or increase type will reduce the time constant in the detonation amplification circuit, as explained in the prior applications. A varistor 197 can be connected across the winding of relay 198 to protect the time constant reducing circuit from excessive peak inverse voltage.

When the test engine knock reaches standard intensity no further compression ratio change pulses are produced and relay 160 will time out, returning its armature 163 to the illustrated position. This closes a solenoid stepping circuit through step 3 contact of deck 1, armature 163, contacts 202, step 2 contact of deck 3 and return lead 199, bringing the stepping switch to the next or mixture-leaning position.

In the mixture-leaning position deck 5 connects an energizing circuit through its step 3 contact to the down winding of the carburetor motor 14. This circuit is completed through switch 193 which is closed whenever the liquid level in the engine carburetor is within the range prescribed by the ASTM Research and Motor methods.

After some lowering of the fuel level the low knock intensity switch 101 closes. This establishes another solenoid stepping circuit through step 4 contact of deck 1, switch 101, step contact 3 of deck 3, and return lead 199. Rotary switch 112 thereupon steps to the next or mixture-enriching position. In the mixture-enrichening position the carburetor liquid level is raised by two phases of operation. Continuous raising of the level occurs first by energizing the up-winding of the carburetor motor 14 through deck 5 and its step 4 contact, lead 184, normally closed delayed opening thermal switch 179, lead 186 and deck 7. At the same time the winding of relay 170 is energized from line 186, motor operated cycling switch 180 has its cycling initiated and normally open delayed closing thermal switch 178 heater element is energized so that its contacts will close in about five seconds.

Switch 179 remains closed for a short period, typically 20 to 30 seconds, after which it opens, the carburetor motor stops raising the fuel level and relay 170 is de-energized. Like relay 160, relay 170 energizes without delay but upon de-energization does not return to the illustrated position until expiration of a pre-set time delay which can be 40–45 seconds or thereabouts. The continuous elevating action of the carburetor motor has caused the maximum knock switch 250 to be under the control of the knock intensity signal which has begun to increase as the air-fuel mixture richened.

The up-winding of the carburetor motor in this second phase of operation is under the control of the maximum knock switch as described in the prior applications, which switch is in series with the cycling switch 180 that alternates 2 seconds closed and 8 seconds open, for example.

The carburetor liquid level is accordingly further raised in intermittent steps until knock intensity stops increasing and the maximum knock switch opens to show that the fuel level for maximum knock has been reached. Each time the fuel level is raised through the action of switches 180 and 250 relay 170 is momentarily re-energized so that it must restart its time delay cycle preventing it from timing out before maximum knock fuel level is established.

After maximum knock is reached and switch 250 opens, relay 170 times out, returning its contacts 171 to the closed position. Before thermal switch 178 cools off enough to open, the stepping switch 112 is stepped twice by a solenoid energizing circuit through step 6 terminal of deck 1, lead 191, thermal switch 178, contacts 171, step 4 and step 5 terminals of deck 3, and return lead 199. As the rotary switch goes through the first of these two steps, deck 5 through its step 5 terminal energizes the winding of relay 160 so that after the second of these two steps the equipment is ready for a final compression ratio search.

The final compression ratio search is just like the initial search except that at its termination the closing of relay contacts 162 causes the rotary switch to step three times. This is effected by a solenoid energizing circuit through step 9 terminal of deck 2, contacts 162, step 6, 7 and 8 terminals of deck 3, and return lead 199.

Lights L1, L2, L3, L4 and L5 are lit through deck 6 and step-down transformer 196 if desired, to indicate the four engine control positions and the completion of the test cycle. Light L5 can also be in parallel with the cycle timer of the computer 28 of FIG. 1 to effect automatic adjustment of the blending valve. Also in parallel with light L5 there can be placed a delay solenoid (not shown) connected to operate start switch 200 so as to begin another test cycle after a few seconds delay that allows for the completion of any needed adjustment of the blending valve. The parallel circuitry described above could also be connected from a suitably positioned contact on deck 5.

It is not necessary to rely solely on compression ratio changes for controlling the blending. Changes in knock intensity at a fixed compression ratio can be used instead. When the blending does not materially affect the fuel-to-air ratio required for maximum knock, the knock intensity can be measured at a fixed fuel-to-air ratio and variation of knock intensity used to make compensatory changes in the blending. Alternatively, where a fixed fuel-to-air ratio is suitable changes in compresssion ratio can be used to control the blending but these changes can be measured in a single compression ratio search. One of the compression ratio search steps and all the fuel-to-air mixture searches can then be eliminated from the testing sequence of FIGS. 1 and 2 to greatly simplify the apparatus and shorten the test and control lag time.

FIG. 3 illustrates an arrangement for automatically controlling blending by knock intensity measurements alone. The test engine 10 here has its detonation meter 18 directly connected to a recorder and controller 81, the controller portion of which can be identical with the computer 28 of FIG. 1. The generation of comparison and correction pulses by the controller can in turn be controlled by a timer 83 that also controls a selector connected to rotate carburetor selector valve 87 to different carburetor bowls 50, 54, 55 and 57. Bowl 50 supplies samples of the blended fuel, as in the construction of FIG. 1, and bowl 54 supplies standard fuel to be matched by the blending. Bowls 55 and 57 supply reference fuels such as blends of pure 2,2,4-trimethyl pentane (isooctane) with n-heptane or tetraethyllead.

The timer 83 is arranged to connect the controller for operating blending valve 30 when the selector connects the engine carburetor to the blending sample bowl 50. The operation of the valve may be direct where the valve is actuated by an electric motor or through an electric-to-pneumatic converter as in FIG. 1, where the valve is pneumatically actuated.

The timer 83 can be arranged to regularly shift the carburetor selector valve to bowls 54, 55 and 57, at which times it disconnects the controller from the blending valve. At those times when bowl 54 is used the recorder merely makes a record of the knock intensities measured. When bowl 55 or 57 is in use the controller is connected to re-evaluate and if necessary adjust its own set point. The reference fuels in bowls 55 and 57 can be utilized at their fuel-to-air mixture ratio corresponding to maximum knock, as by presetting the respective fuel or bowl levels, to give knock intensities which can be used as checks for the standard fuel and/or the blended fuel, particularly when the knock intensities of the reference fuels bracket the desired knock intensity.

Instead of having a purely electrical arrangement for balancing a control element with a set point, it can be made partially or completely mechanical, pneumatic, hydraulic, magnetic, or of any other form.

The construction of FIG. 4 has a mechanical comparison and differential computer indicated generally at 400. This can be of the usual type such as that described in pages 42 and 43 of Minneapolis-Honeywell Regulator Co. Catalog C15-2, copyright 1957 by that company. It has a pen-carrying indicator arm 402 journaled at 404 and rotated around that journal by a balancing motor 406 that received electrical balancing signals from a balancing circuit 408 of any suitable type such as those shown and described on pages 6 and 7 of the above-identified catalog to which reference can be made for a more complete description. Suffice it to say that the balancing circuit can take a dc voltage such as supplied by the detonation meter 18 of an ASTM test engine 10, measure its difference from a standard voltage, convert that difference to an ac power output having an intensity that varies in accordance with the measured dc difference, and supply that power output to one winding of a variable speed reversing induction motor. A standard ac power supply in synchronism with the foregoing variable power ac supply is delivered to the reverse winding of the motor. Variation in the intensity of the variable power supply with respect to the standard ac supply will then cause the motor 406 to turn in one direction or the other.

A set point index arm 410 is pivoted at 412 and is secured to a plate 414 which in turn carries a pivot 416 supporting one end of a differential lever 418. A differential link 420 interconnects the other end of the differential lever with the corresponding end of an indicator lever 421 that rotates about journal 404 with the indicator arm 402.

A control link 422 connected to the differential lever 418 is so arranged that when both the indicator arm 402 and the set point arm 410 are rotated together around their pivots, the control link does not move. However, when one of these arms moves with respect to the other, the control link 422 is pulled up or pushed down.

The set point arm 410 is made adjustably positionable by a knob 424 which through a gear train tilts the plate 414 about its pivot 412 and in this way raises or lowers the pivot 416 for the differential lever. Inasmuch as set point arm 410 tilts with plate 414, the set point position is also changed. The plate as illustrated has a sector gear or rack 423 in a different plane than that in which it is pivoted at 416, but other constructions can also be used. A second balancing motor 426 is shown as connected to automatically operate set point adjustment under the control of the balancing circuit 408. With such motor control of the set point, the knob 424 can be eliminated if desired.

Movements of the control link 422 are translated into variations in air pressure in an air line 428, by transmitting this motion to a movable flapper 430 located very close to the mouth of the line. The resulting changes in pressure are amplified by a pilot valve 460 into larger changes in the principal air line 432 which operates a pneumatic valve 434 to adjust the blending.

By supplying the test engine 10 in the construction of FIG. 4 with samples of blended fuel, variations in knock intensity can be used to control changes in the amount of antiknock fluid or the like blended into the fuel. Intermittent or continuous operation of the balancing motor 406 by circuit 408 can then be effected with a selector 436, for example, so arranged to periodically shift the test engine fuel supply to a standard fuel, at the same time switching the operation of the balancing circuit 408 so that it controls balancing motor 426 instead of balancing motor 406. This will enable adjustment of the set point arm 410 so that it properly indicates the position from which the indicator arm 402 is to show departures.

To increase stability and reduce hunting, the apparatus of FIG. 4 also includes a stabilizing assembly 440 that has a pair of large liquid-filled bellows 441, 442 with the exterior of bellows 441 exposed to the control pressure in line 432. The second bellows 442 is under the compressive effect of a mechanical spring 444. Within the foregoing bellows are smaller bellows 451, 452 respectively each secured to the opposite end of a balancing rod 446 that is connected to move the flapper support. The liquids within the large bellows and around the small bellows have a transfer conduit 448 with a controllable aperture to gradually equalize the pressures in the respective large bellows.

Any change in control pressure in line 432 will accordingly not only tend to restore control arm 402 to the position of the set point arm, but will slowly cause a shifting of the flapper 430 with respect to nozzle 428 so that the changed control pressure tends to maintain itself.

The flapper can also be arranged to have its pivot 450 moved toward or away from the nozzle 428 so as to vary the range of pressure change caused by movements of the control link. To this end the flapper pivot is shown as carried on a block 453 that can be raised or lowered as by a rack and pinion gear operated by dial 454.

The entire stabilizing assembly 440 can be omitted, if desired, and hunting controlled by other techniques such as delaying changes in control pressure for a time that permits previous changes to take full effect on the blending. In as much as the measuring lag may be as much as 8 or 10 minutes or somewhat more where a full anti-knock search sequence is used, the sampling of fuel may be made at corresponding intervals.

In order to make sure that gradual drifting of the test engine or the like will not cause the index arm 410 or corresponding set point slidewire settings to reach a limit of their travel and therefore be unusable, the automatic apparatus of the present invention can also be provided with self-centering mechanism. One such structure is shown in FIG. 5, where a set point slidewire 502 is connected for resetting as by shaft 504 of the compression ratio motor for the ASTM engine. The resetting is controlled by a magnetic clutch 506 energized at the proper times by sequencer 536 that can operate in the manner described for the selector 436 in the construction of FIG. 4.

Automatic centering is arranged by providing a two-phase reversing motor 510 with its opposite windings each connected in series through separate switches 511, 512 to a power supply lead 514 from the sequencer. A centering cam 516 is connected for rotation by a shaft 518 connecting it to setpoint slidewire 502 and the reversing motor, the cam having high and low lobes coacting with switches 511, 512 so that the reversing motor is rotated in one direction or the other until the centering cam is brought to the position at which both switches are open. The cam lobes are so arranged that both switches are open only when the cam is in the slidewire centering position.

Where the slidewire 502 is of the multiple turn variety a gear reducer 520 can be connected between the slidewire and the centering cam and arranged so that one turn of the cam corresponds to the movement of the set point over the entire range of travel along the slidewire. An auxiliary clutch 522 can also be provided for the reversing motor 510 to disconnect the two phase motor during operation of the slidewire 502 by the compresion ratio motor.

Instead of having a centering mechanism for the set point element and having that element automatically controlled, the set point element can merely be in the form of a member fixed at a predetermined value setting. Such setting can for example be the mid-point or other convenient point of the control indicator such as the control slidewire or control arm.

Figure 6:
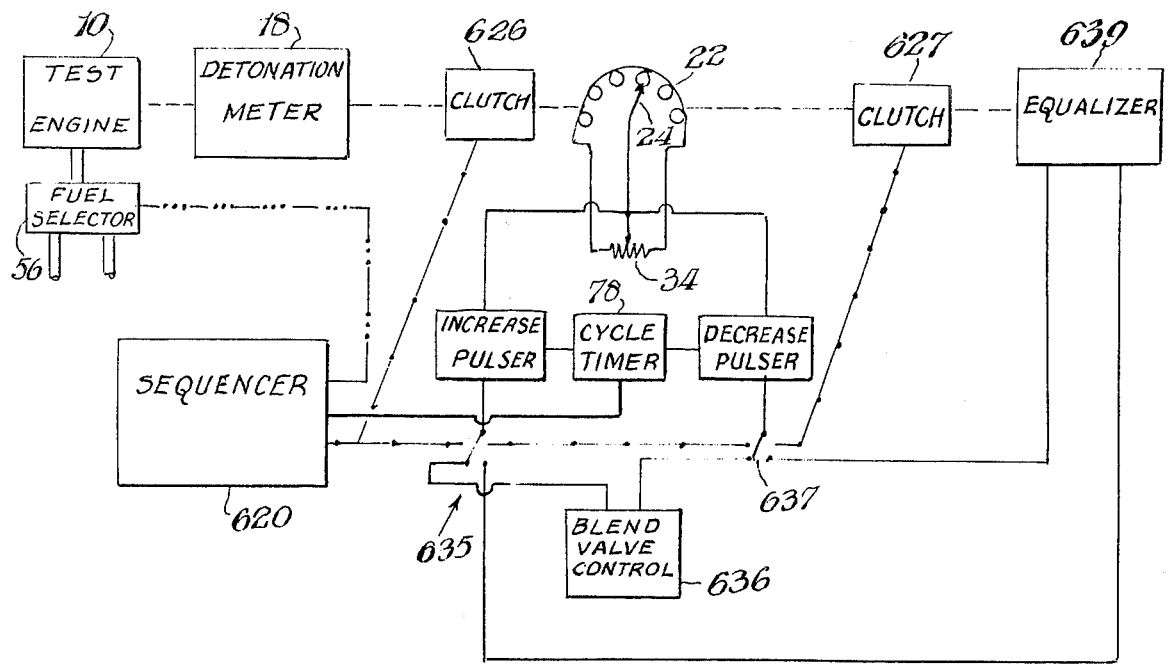
FIG. 6 is a schematic illustration of still another modification of automatic blending apparatus pursuant to the present invention.

FIG. 6 illustrates this type of operation. The apparatus here shown is of the knock intensity control arrangement, as is the apparatus of FIG. 3. It has a test engine 10 with a fuel selector valve 56 and a detonation meter 18 connected to operate the arm 24 of a control slidewire 22 through a remotely controllable clutch 626. A set point slidewire 34 is balanced against the control slidewire, and connected to increase and decrease pulsers under the influence of cycle timer 78, as in FIG. 1. The outputs of the pulsers are fed through switches 635, 637 that shift their pulses between a blend valve control 636 and a slidewire equalizer 639. A second clutch 627, also remotely controllable, selectively connects the equalizer to the control slidewire arm 24.

Sequencer 620 is arranged to operate fuel selector 56, clutches 626, 627, cycle timer 78, and switches 635, 637. The apparatus can be placed in operation as by setting the tap of the set point slidewire 34 at its mid-point, and then causing the sequencer to select a reference fuel, disengage clutch 626, engage clutch 627, and shift switches 635, 637 to their equalizer contacts. A few minutes running of the test engine will then produce a steady detonation meter signal while periodic cycle timer operation causes the equalizer, which need be nothing more than a reversing motor as in the construction of FIG. 5, to bring the control slidewire arm 24 to its mid-point position. To make sure the detonation meter is operated in an appropriate range, the test engine can have its compression ratio and fuel-to-air ratio manually or automatically adjusted.

The sequencer then operates the fuel selector to deliver blend fuel to the test engine while clutch 626 is engaged, clutch 627 disengaged, and switches 635, 637 shifted to their blend valve control terminals. Continued operation of the test engine then causes the blending valve to so control blending as to keep the detonation meter output at a value that holds control slidewire arm 24 at its midpoint. After a period of such blending control that can range from 10 minutes to an hour or more, the sequencer shifts back to standard reference fuel and restores the control slidewire arm to its midpoint. Such restoration will involve no slidewire movement unless the test engine characteristics have changed, as by build-up of combustion chamber deposits, so that the detonation meter signal level is shifted from where it should have been to properly indicate the anti-knock rating of the blended fuel. Where such deposit build-up causes higher knock intensities, the apparatus can automatically increase the antiknock rating of the blended fuel even though no such increase is needed. However the periodic equalizing of the control slidewire arm will compensate for the changed output of the detonation meter and assure proper blending. Either the fixed or controllable set point arrangements can be used with any of the automatic controls, whether of the compression ratio type as in FIG. 1, or the knock intensity type as in FIG. 3.

The blending apparatus of the invention can also have warning devices such as a bell that sounds to indicate that knock intensities are getting severe enough to endanger engine operation, or are getting too faint to be useful. It is in fact preferred to shut down the apparatus and correct the cause of drift before they reach such extremes. The apparatus can also have automatic compression ratio searching, as in the construction of FIG. 1, to thereby automatically compensate for some of the possible drift in the engine operation conditions.

A warning arrangement can also be provided to indicate when a blend ingredient supply is called for at a rate too high for proper operation. For example there is usually a ceiling on the maximum amount of antiknock compound permitted in a fuel and the warning device can be connected to call attention to a valve position that reaches or exceeds such maximum. A similar warning can indicate when there is a material drop in pressure in a blend ingredient line controlled by an automatically operated valve, indicating that the flow through that line is not being properly controlled by the valve. A similar warning arrangement can indicate when a controlled valve is completely closed.

Instead of having analog signal systems, the blending control can operate with digital signals, as for example pulses or alternating currents generated at repetition rates or frequencies that vary in accordance with compression ratio or knock intensity measurements and are compared with a standard such as the omnipresent 60 cycle power system. Differences between the signal frequency and the standard frequency can then operate the blending controls.

Sampling of fuel for the blending control arrangement that uses the compression ratio measuring system (as in FIG. 1) need not be maintained at all times at the rapid flow rate, but can be intermittent. For this purpose a limiting valve can be inserted in the sampling conduit 42 and it can be automatically opened wide by the sequencer 20 whenever a compression ratio determining sequence is completed. Before completions the limiting valve can be closed to a position that barely allows sufficient flow to operate the engine and keep the fuel level in the carburetor from dropping.

The knock intensity control system (as in FIG. 3) gives much faster control and is better used with a rapid sampling flow.

The compression ratio control arrangement can also be operated with fuel mixture test excursions carried out only once in every two, three, four or more measuring cycles. Indeed, when the fuel is sufficiently uniform to have no significant change in the mixture ratio that provides maximum knock, these test excursions can be entirely eliminated.

It is a feature of the present invention that the automatic blending or alkyllead compounds like tetraethyllead into refinery gasoline streams seems to use the antiknock values of the alkylleads somewhat more economically than prior art nonautomatic systems. Tests have shown that the automatic system requires about 2/10 of a gram of tetraethyllead less per gallon to reach specification octane numbers.

The automatic blending of the present invention also effects a highly accurate and closely reproducible blending operation. In general, the compression ratio control system such as illustrated in FIGS. 1 and 2, produces a blended product having a research octane number within ± 0.3 of any predetermined value. The knock intensity control system, as in FIG. 4, maintains a blending to within about ± 0.2 of a research octane number.

Obviously many modifications and variations of the present invention are possible in the light of the above teachings. It is, therefore, to be understood that within the scope of the appended claims the invention may be practiced otherwise than as specifically described.

What is claimed is:

1. In an apparatus for sampling a liquid for test purposes and providing the sample at a predetermined elevation, a relatively small upright container having means for continuously supplying it with the liquid being sampled at a rate greater than required for testing, an outlet in its lower portion for connection to a testing means, and a suction tube projecting into the interior of the container from its upper portion for sucking out excess liquid and thereby defining a level for the liquid in the container.

2. The combination of claim 1 in which the suction tube is threaded through the top of the container and has a rotary connector that provides a connection to a suction line and also provides for rotation of the suction tube with respect to the container top without interfering with the suction.

3. The combination of claim 1 in which the container has transparent walls.

4. A method of sampling a moving stream of liquid for test purposes, which method comprises the steps of withdrawing the liquid from the moving stream at a withdrawal rate of about 300 to 500 milliliters per minute, continuously delivering the withdrawn liquid to a relatively small upright container a distance away, sucking off liquid from the upper portion of the container to define a liquid level therein, and supplying liquid from the lower portion of the container to a testing means.

5. The combination of claim 4 in which the liquid is gasoline and the testing means is a knock test apparatus.

6. An apparatus for making repeated knock ratings of a fuel, said apparatus including automatic knock measuring equipment having a test engine, an indicator to show the relative rating of a fuel sample by that engine, a standard reference control, means for originally setting the indicator at a predetermined portion of its range, and automatic compensating mechanism connected to the engine to periodically cause it to measure the knock of a standard fuel and to automatically adjust the indicator so that the rating of the standard fuel corresponds with the standard reference control to compensate for drift of the automatic measuring equipment.

7. An automatic gasoline testing apparatus having a knock-testing engine, sampling means connected to selectably receive samples of test gasoline and of a standard fuel and supply the samples to the engine, an indicator to show the relative knocking characteristics of the engine when supplied with the different fuels, the indicator having a predetermined range of movement, and automatic compensating mechanism connected to shift the engine operation from the test gasoline to a standard fuel and to automatically adjust the indicator so that its indication for the standard fuel is at an intermediate portion of its range.

8. The combination of claim 7 in which the indicator is connected to show the compression ratio of the test engine.

9. The combination of claim 7 in which the indicator is connected to show the intensity of knocking in the test engine.

10. The combination of claim 7 in which the apparatus further includes automatic control elements connected to repeatedly operate the indicator without intervening check of fuel-to-air ratio in the fuel-air mixture supplied to the engine.

* * * * *